United States Patent [19]

Marks

[11] 4,061,770
[45] *Dec. 6, 1977

[54] FLOWABLE, AQUEOUS PESTICIDE COMPOSITIONS OF IMPROVED ACTIVITY

[75] Inventor: Alfred F. Marks, Mentor, Ohio

[73] Assignee: Diamond Shamrock Corporation, Cleveland, Ohio

[*] Notice: The portion of the term of this patent subsequent to Apr. 6, 1993, has been disclaimed.

[21] Appl. No.: 677,141

[22] Filed: Apr. 15, 1976

[51] Int. Cl.² ............................................. A01N 9/20
[52] U.S. Cl. ............................. 424/304; 71/DIG. 1; 424/173; 424/363
[58] Field of Search .................. 424/173, 304, 363; 71/DIG. 1

[56] References Cited

U.S. PATENT DOCUMENTS

| | | | |
|---|---|---|---|
| 3,020,206 | 2/1962 | Patton et al. | 536/1 X |
| 3,948,636 | 4/1976 | Marks | 424/304 X |

Primary Examiner—Allen J. Robinson
Attorney, Agent, or Firm—Helen P. Brush

[57] ABSTRACT

An aqueous, flowable composition containing a high concentration of a solid, essentially water-insoluble, pesticidally-active component homogeneously dispersed therein is prepared by wet-milling the active component in an aqueous matrix together with dispersants. The flowable, pesticidal composition obtained exhibits significantly improved pest control by comparison to that possessed by similar compositions containing air-milled, pesticide components of like average particle size.

7 Claims, 2 Drawing Figures

FLOWABLE, AQUEOUS PESTICIDE COMPOSITIONS OF IMPROVED ACTIVITY

BACKGROUND OF THE INVENTION

This invention relates to a method for preparing an aqueous, flowable pesticide concentrate of improved activity which comprises wet-milling the essentially water-insoluble active component in an aqueous medium, and more particularly, relates to the improved flowable pesticide composition produced by wet-milling.

A flowable, aqueous pesticide composition has recently been developed which eliminates the handling and storage problems which have previously been encountered in using wet-table powders and other earlier formulations of water-insoluble pesticides which are likewise sparingly soluble in organic solvents. This composition which is disclosed in U.S. Pat. No. 3,948,636, issued Apr. 6, 1976, is a homogeneous, aqueous suspension of at least one solid, essentially water-insoluble pesticidally-active component, together with a combined dispersing system therefor which is composed of a minor quantity each of a heteropolysaccharide gum and at least one nonionic surfactant. This composition is completely dilutable with water for easy application. It is further characterized by excellent storage stability, even though it may contain extremely high concentrations of finely-divided active ingredient, e.g., up to and including 6 pounds of pesticide per gallon (0.72 kilograms of active ingredient per liter).

SUMMARY OF THE INVENTION

It has now been found that if a flowable pesticide composition is prepared by grinding the active ingredient and its dispersing components together in the aqueous medium, i.e., by a wet-grinding process, rather than by merely blending a preground active component and adjuvants together with stirring, the flowable pesticide composition produced exhibits significantly greater activity than its blended counterpart. The greater activity of the wet-milled material is obtained even though the average particle size of the pesticidally-active component therein is the same as or even greater than that of the physically blended material.

DESCRIPTION OF THE PREFERRED EMBODIMENTS

Figure 1:
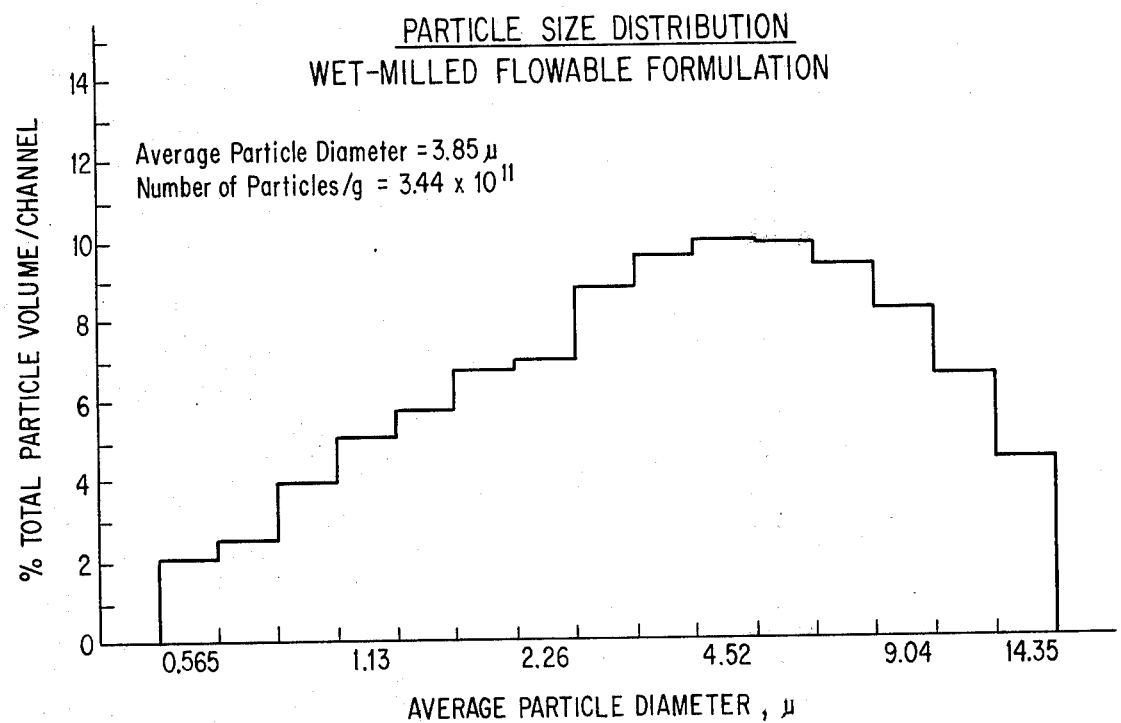

The nature of the components and the quantities of each which constitute the composition of this invention are the same as those disclosed in the above-listed patent, U.S. Pat. No. 3,948,636, which disclosure is incorporated herein by reference. Thus, the composition herein generally may contain, by weight,
1. 10–60% of at least one finely-divided essentially water-insoluble pesticide;
2. 1–10% of a nonionic surfactant;
3. 0.02–1.0% of a heteropolysaccharide gum;
4. 0–10% of an anticaking agent;
5. 0–5% of an antifoaming agent; and
6. 0–10% of a freeze-point depressant, with water being used in sufficient quantity to provide, in combination with the other ingredients, 100 parts of finished composition.

As used herein, the terms "active", "pesticidally-active", "pesticide", "pesticidal", and the like, are each intended to refer to toxicants and to biological compositions containing these chemicals which are effective in killing, preventing, or controlling the growth of undesirable pests, e.g. plants, insects, mice, microorganisms, algae, fungi, bacteria, and the like, said chemicals and compositions being commonly known as insecticides, miticides, bactericides, algacides, fungicides, nematocides, herbicides, etc. The toxicant chemicals employed in the flowable pesticide formulations of this invention are essentially insoluble in water, that is to say, they are typically less than 1 percent water-soluble. Examples of specific known toxicants which suitably may be employed as such in the compositions of this invention are disclosed in the previously described U.S. Pat. No. 3,948,636, which disclosure likewise is incorporated herein by reference.

Compositions in accordance with this invention which exhibit singularly improved activity at the present time are insecticidal and fungicidal formulations. In particular, fungicidal formulations containing, by weight, from 10 to 60 percent DACONIL (tetrachloroisophthalonitrile) as the active ingredient exhibit optimum activity, and for this reason, specific reference will be made hereinafter to these particular formulations. Such reference, however, is not to be construed as limiting in any way the present invention to the preparation and use of formulations of tetrachloroisophthalonitrile fungicide only.

As described previously, the improved flowable pesticide compositions of this invention, like those set forth in U.S. Pat. No. 3,948,636, contain at least one finely-divided, essentially water-insoluble pesticide, e.g. fungicide, and as necessary dispersants therefor, a nonionic surfactant and a heteropolysaccharide gum.

As the nonionic surfactant component, specific suitable compounds include, for example, the ethoxylated alkylphenols, aliphatic alcohols or fatty acids; ethoxylated anhydrosorbitol esters; and ethoxylated polyoxypropylene glycols.

The heteropolysaccharide gum component, also designated in the art as a xantham gum, is a high molecular weight, linear exocellular material prepared by the action of bacteria of the genus Xanthomonas on carbohydrates. Preparation of heteropolysaccharides suitably used herein is described in greater detail, for example, in U.S. Pat. No. 3,020,206.

It is to be understood, of course, that other adjuvants such as freeze-point depressants, anticaking agents, and antifoaming agents may optionally be incorporated into the composition when specific storage and/or use conditions of the composition warrant their use.

To prepare the composition, the active ingredient, the dispersants and other optional components as desired are homogeneously ground together in the aqueous medium in a chamber by the shearing action of rotating metal balls in contact therewith, according to procedures normally practiced at the present time in wet-milling operations. Any commercially available wet-milling equipment which preferably has a pumping system to maintain circulation of the mix during the grinding process generally may suitably be used herein. Examples of such equipment are the series of Attritors manufactured by Union Process, Inc., Akron, Ohio.

The particular particle size of the active ingredient to be formulated is not critical to the success of the milling operation. Highly active formulations can easily be prepared from compounds of widely varying particle size. For example, tetrachloroisophthalonitrile fungicide, as commercially manufactured, is a highly crystalline material with a particle population ranging typically from about 5 microns to over 15 microns in size. Heretofore, when physically blending flowable formulations of this fungicide, it has usually been necessary to first air-mill, hammer-mill or otherwise conventionally pulverize the active ingredient so as to formulate and apply it in finely divided particulate form. Average particle sizes attainable by such pulverizing procedures are generally 3–5 microns.

In practice herein, the wet-milling operation is continued for a sufficient period of time to provide a flowable pesticide suspension wherein the active ingredient has an average particle size range of 1–5 microns, more preferably, a range of 1.5–4.0 microns. To attain such average particle sizes, grinding times will vary widely, of course, e.g. from 1 to 30 hours, depending upon such factors as the volume of the formulation being ground, the percentage of active ingredient charged and the capacity of the particular milling apparatus employed.

As will easily be recognized by those skilled in the art, the order of charging the ingredients to the milling apparatus is somewhat critical so as to avoid lumping of the active ingredient or of any other optional solid adjuvants incorporated. In one method practiced herein, the water, surfactant and any other liquid components, e.g. antifoaming agents or alkylene glycol freeze-point depressants, are charged initially, followed by addition of the active ingredient. Milling of the added components is then conducted for a sufficient time to assure a homogeneous mixture, after which the heteropolysaccharide gum is added. With continued milling, the mixture thickens significantly as the gum component becomes uniformly admixed.

Alternatively, of course, all of the components of the formulation initially may be incorporated into the water with stirring as typically carried out when preparing physically blended flowable formulations. The flowable mixture thus prepared may then be charged to the milling apparatus and ground according to this invention.

The particle population of the wet-milled pesticide composition of this invention is determined using a Coulter Counter, manufactured by Coulter Electronics, Inc., Hialeah, Fla. By "particle population" is meant, e.g. the average particle size (diameter) of the dispersed active ingredient, the number of particles per gram of formulation, the volume (or weight) percentages of particles of active ingredient within each of the various orifices (channels) of the Counter, etc. This method of determining average particle size and particle distribution will be easily recognized by those knowledgeable in the art of assessing physical dimensions of dispersed solids.

By comparison to its physically blended counterpart, a wet-milled pesticide composition of this invention appears to have a more even distribution, having more small particles and likewise more particles in the largest category, on a volume (or weight) basis, than the blended formulation.

Figure 2:
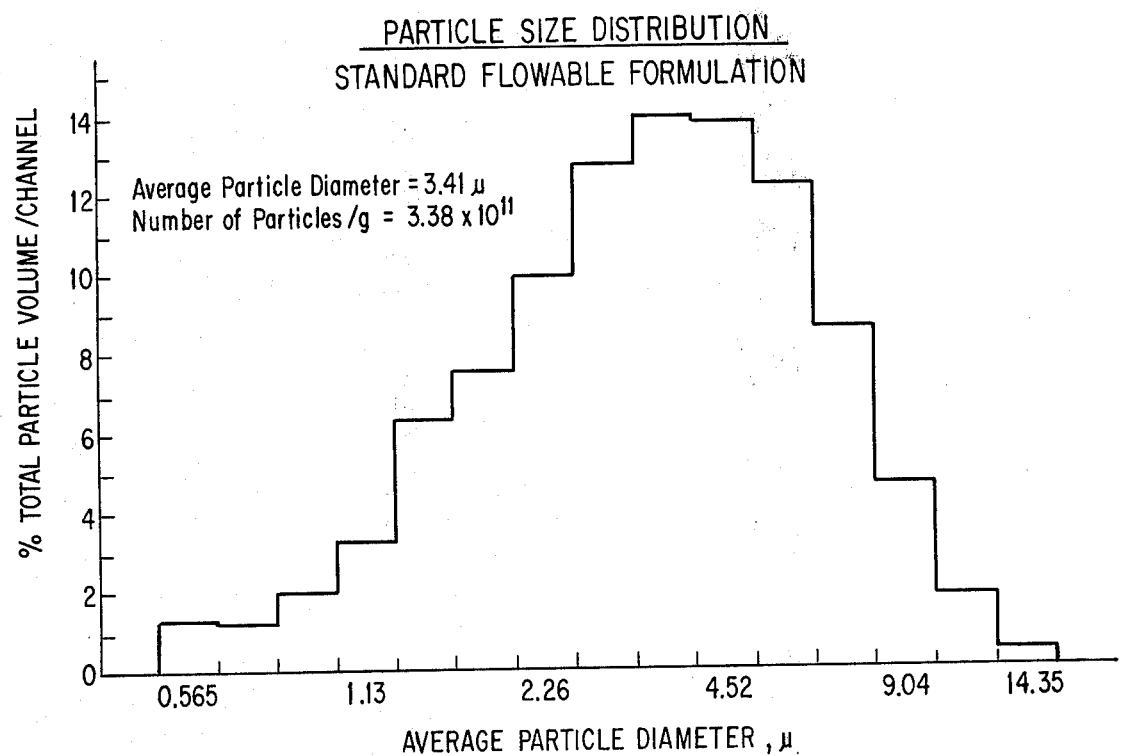

The accompanying FIGS. 1 and 2 illustrate the particle distribution curves obtained by plotting particle size values obtained upon analyzing the wet-milled formulation of Example 1 below and also a physically blended formulation of similar composition on the Coulter Counter. As can be seen from these curves, the particle size parameters of the two formulations are similar, the average particle diameter of the wet-milled material being somewhat larger. The overall particle size distribution patterns of the two formulations are noticeably different, however. That of the wet-milled formulation has no defined peak like that of the physically blended (standard) material, and indicates that the particles of active ingredient in the wet-milled formulation are more uniform in size and distributed more evenly than in the corresponding physically blended formulation.

For a fuller understanding of the nature of this invention and the methods for carrying it out, the following illustrative examples are given.

EXAMPLE 1

A wet-milled fungicide composition of this invention is prepared from the following formulation:

|  | % by weight |
| --- | --- |
| Tetrachloroisophthalonitrile | 54.00 |
| Alkylaryl polyether alcohol[1] | 5.20 |
| Heteropolysaccharide gum | 0.10 |
| Propylene glycol | 3.70 |
| Cab-O-Sil M-5[2] | 1.50 |
| Antifoam FG-10[3] | 0.25 |
| Water | 35.25 |

[1]TRITON X-100 surfactant - Rohm and Haas Co.
[2]Anhydrous $SiO_2$ anticaking agent - Cabot Corp.
[3]Silicone emulsion - Dow Corning Corp.

An Attritor, Model Q-1, equipped with a circulating pump is first charged with steel balls 3.2 mm in diameter, and then the water, alkylaryl polyether alcohol, propylene glycol and other antifoamer components are added and agitation is started. The active ingredient is slowly added to the circulating liquid mixture, after which milling is continued for at least 2 hours at ambient temperature. The heteropolysaccharide gum is added and the mixture thickens gradually with continued grinding. The anticaking agent is added and blended thoroughly into the mixture. After 3 hours total milling, the composition is removed from the grinding chamber.

For comparison purposes, a similar formulation is prepared as described in Example 2 of U.S. Pat. No. 3,948,636, using preground active ingredient. In this procedure, all of the components other than the fungicide are incorporated into the water at ambient temperature after which the fungicide component is incorporated with stirring.

The particle size distribution profile of each formulation is determined in a Coulter Model TA11 Counter equipped with a 30 micron orifice, using a 2% electrolyte elutriation medium with the following particle classification results:

TABLE 1

| Counter Channel | Channel Average Particle Diameter, μ | Percent Particle Volume/Channel | |
| --- | --- | --- | --- |
| | | Wet-Milled Formulation | Blended Formulation |
| 16 | 14.35 | 4.42 | 0.49 |
| 15 | 11.39 | 6.63 | 1.78 |
| 14 | 9.04 | 8.21 | 4.62 |
| 13 | 7.18 | 9.40 | 8.62 |
| 12 | 5.70 | 9.80 | 12.20 |
| 11 | 4.52 | 9.98 | 13.84 |
| 10 | 3.59 | 9.54 | 13.99 |
| 9 | 2.85 | 8.81 | 12.77 |
| 8 | 2.26 | 7.01 | 9.96 |
| 7 | 1.80 | 6.77 | 7.54 |
| 6 | 1.43 | 5.76 | 6.29 |
| 5 | 1.13 | 5.10 | 3.25 |
| 4 | 0.897 | 3.92 | 1.98 |
| 3 | 0.712 | 2.57 | 1.29 |
| 2 | 0.565 | 2.08 | 1.36 |

The average particle diameter in each formulation determined from cumulative particle volume percentages is as follows:
Wet-milled formulation = 3.85 microns
Blended formulation = 3.41 microns

EXAMPLE 2

Field Application

The above described wet-milled and physically blended tetrachloroisophthalonitrile formulations are tested to determine their comparative efficiency in controlling *Cercospora arachidicola* Hori and *Cerosporidium personatum* (Berk and Curt) Deight leafspot in peanuts.

Test plots, each consisting of four 15.2 meter rows spaced 6.9 meters apart, are planted to peanuts (*Arachis hypogaea* L. cultivar 'Florunner'). Forty-five days after planting, the plots are sprayed with diluted formulations of each flowable composition containing dosages of active ingredient as shown in the table below. At 14-day intervals thereafter, the sprayings are repeated for a total of 7 applications. Peanut yields are determined by harvesting the two center rows of each plot 145 days after planting. Disease is evaluated 1 week before harvest on 10 vertical stems (runners) removed at random from the center two rows of each plot using the formula: percent infection = leaflets infected ÷ total leaflets × 100. Percent defoliation is determined by first calculating the total number of leaflets (multiplying the number of leaf nodes by 4), then using the formula: number of leaflets lost ÷ total leaflets × 100. The results obtained are as follows:

TABLE 2A

| Dosage Rate | Percent Infection | | | |
|---|---|---|---|---|
| (kg/ha) | 0 | 0.63 | 0.84 | 1.26 |
| Formulation | | | | |
| Wet-milled | 62.8 | 44.2 | 43.7 | 35.3 |
| Blended | 61.2 | 54.6 | 50.4 | 41.6 |

TABLE 2B

| Dosage Rate | Percent Defoliation | | | |
|---|---|---|---|---|
| (kg/ha) | 0 | 0.63 | 0.84 | 1.26 |
| Formulation | | | | |
| Wet-milled | 39.0 | 29.7 | 27.7 | 27.7 |
| Blended | 38.7 | 33.4 | 33.5 | 26.9 |

As the above results indicate, the wet-milled composition exhibits much improved fungicide activity over the physically blended formulation, particularly at lower dosage rates. These results are unexpected and surprising since the average particle size of the wet-milled formulation is larger than that of the physically-blended material.

I claim:

1. A process for preparing a flowable, homogeneous, storage-stable aqueous pesticide composition which comprises successively charging to a chamber equipped with metal balls, water in sufficient quantity to provide, in combination with the other ingredients, 100%, by weight, of finished composition, from 1.0 to 10%, by weight of a non-ionic surfactant, from 0 to 5%, by weight, of a liquid antifoaming agent, from 0 to 10%, by weight, of a freeze-point depressant, and from 10 to 60%, by weight, of an essentially water-insoluble, pesticidally-active component having an average particle size ranging from about 5 microns to over 15 microns; homogeneously mixing the ingredients in the chamber by the shearing action of the rotating metal balls; thereafter adding successively from 0.02 to 1.0%, by weight, of a heteropolysaccharide gum and from 0 to 10%, by weight, of an anti-caking agent and wet-milling the resulting mixture until said gum component is uniformly admixed and the mixture thickens significantly, the total wet-milling time ranging from 1 to 30 hours, the average particle size of the pesticidally-active component in the finished composition being 1.0–5.0 microns.

2. The process of claim 1 wherein the essentially water-insoluble, pesticidally-active component is tetrachloroisophthalonitrile fungicide.

3. The process of claim 2, wherein wet-milling is conducted for a time period of 3 hours.

4. The process of claim 1 wherein the pesticidally active component in the finished composition has an average particle size of 1.5–4.0 microns.

5. A process for preparing a flowable, homogeneous, storage-stable aqueous pesticide composition which comprises mixing in an aqueous medium with stirring, from 10 to 60%, by weight, of an essentially water-insoluble, pesticidally-active component having an average particle size ranging from about 5 microns to over 15 microns, from 1.0 to 10%, by weight, of a non-ionic surfactant, from 0.02 to 1.0%, by weight, of a pg,16 heteropolysaccharide gum, from 0 to 10%, by weight, of an anti-caking agent, from 0 to 5%, by weight, of an anti-foaming agent, and from 0 to 10%, by weight, of a freeze-point depressant, the aqueous medium being used in sufficient quantity to provide, in combination with the other ingredients, 100%, by weight, of finished composition; charging the prepared flowable mixture to a chamber equipped with metal balls and homogeneously wet-milling said mixture by the shearing action of the rotating metal balls in contact therewith until the pesticidally-active component in the composition has an average particle size of 1.0–5.0 microns, the total wet-milling time ranging from 1 to 30 hours.

6. The process of claim 5 wherein wet-milling is conducted for a time period of 3 hours.

7. The process of claim 5 wherein the essentially water-insoluble, pesticidally-active component is tetrachloroisophthalonitrile fungicide.

* * * * *

UNITED STATES PATENT AND TRADEMARK OFFICE
CERTIFICATE OF CORRECTION

PATENT NO. : 4,061,770
DATED : December 6, 1977
INVENTOR(S) : Alfred F. Marks

It is certified that error appears in the above-identified patent and that said Letters Patent are hereby corrected as shown below:

Claim 5, at the end of line 8, delete the term "pg, 16".

Signed and Sealed this

Fourth Day of April 1978

[SEAL]

Attest:

RUTH C. MASON
Attesting Officer

LUTRELLE F. PARKER
Acting Commissioner of Patents and Trademarks

Disclaimer 4,061,770.—*Alfred F. Marks,* Mentor, Ohio. FLOWABLE, AQUEOUS PESTICIDE COMPOSITIONS OF IMPROVED ACTIVITY. Patent dated Dec. 6, 1977. Disclaimer filed Feb. 18, 1982, by the assignee, *Diamond Shamrock Corp.*

Hereby enters this disclaimer to claims 1–7, inclusive of said patent.

[*Official Gazette April 13, 1982.*]